(12) United States Patent
Boukas

(10) Patent No.: US 7,169,354 B2
(45) Date of Patent: Jan. 30, 2007

(54) PROTEIN DETECTING DEVICE

(76) Inventor: Alex Boukas, 14695 Main Rd., Mattituck, NY (US) 11952

( * ) Notice: Subject to any disclaimer, the term of this patent is extended or adjusted under 35 U.S.C. 154(b) by 75 days.

(21) Appl. No.: 10/995,842

(22) Filed: Nov. 22, 2004

(65) Prior Publication Data
US 2006/0110286 A1 May 25, 2006

(51) Int. Cl.
G01N 21/00 (2006.01)
G01N 31/22 (2006.01)
B01L 3/02 (2006.01)

(52) U.S. Cl. .............................. 422/58; 422/56; 422/57; 422/100

(58) Field of Classification Search .................... 422/58
See application file for complete search history.

(56) References Cited

U.S. PATENT DOCUMENTS 5,238,649 A * 8/1993 Nason .......................... 422/58
5,266,266 A * 11/1993 Nason .......................... 422/58
5,339,829 A * 8/1994 Thieme et al. ............... 600/573
6,022,326 A * 2/2000 Tatum et al. ................. 600/573

* cited by examiner

Primary Examiner—Jill Warden
Assistant Examiner—Lore Janet Ramillano
(74) Attorney, Agent, or Firm—Thomas A. O'Rourke; Bodner & O'Rourke, LLP

(57) ABSTRACT

A protein detecting device is disclosed. The device includes a reagent reservoir that is squeezable. The reagent reservoir has an end portion with a with a tubular member extending therefrom. This tubular member is hollow and in communication with the reservoir. The tubular member has an open end opposite the reservoir and has a cone shaped gasket in its open end. The cone shaped gasket has its base connected to an elongated member extending from the open end of the tubular member. The elongated member has a micro-brush at its end.

19 Claims, 4 Drawing Sheets

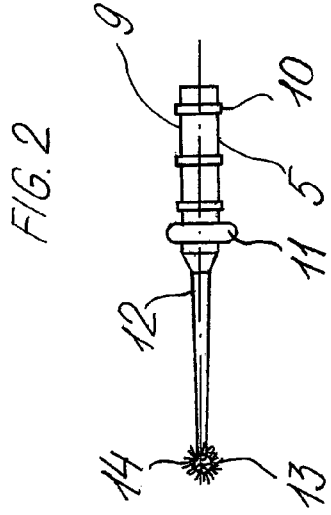
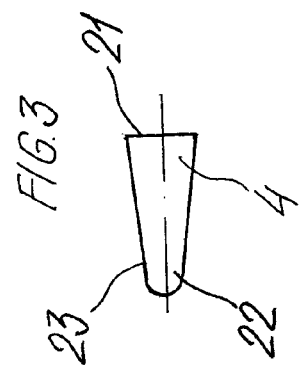
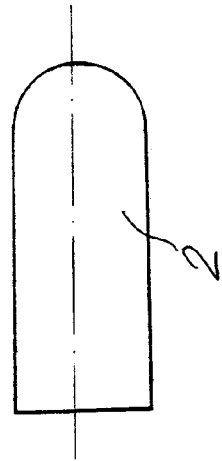
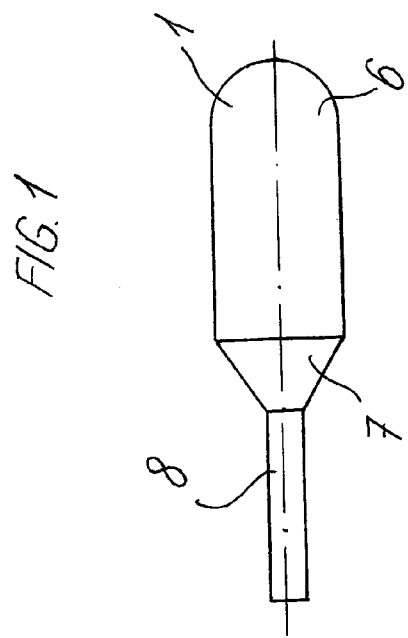
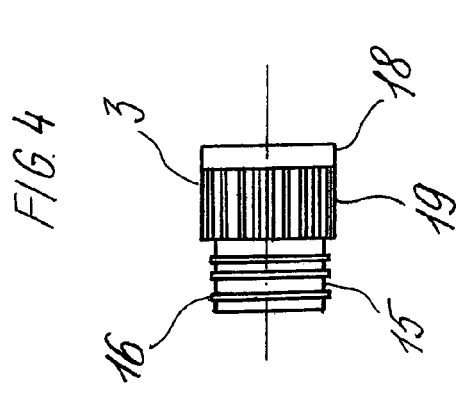

B-direction

A-direction

PROTEIN DETECTING DEVICE

FIELD OF THE INVENTION

The present invention relates to an apparatus that allows a user to conduct an assay by combining two or more materials in a single container. Particularly, this invention provides convenient, fast and safe way to identify the presence of a protein containing substance such as a solid, a powder or a liquid using a reagent capable of giving an indication, usually visual, such as changing color when such reagent is exposed to the protein-containing substance.

BACKGROUND OF THE INVENTION

This invention is directed to a device that may be used in wide variety of assays. Generally, the invention allows a user to mix one or more chemical reagents with a tested material. For example, the device may be used to mix chemical substances with reagents when the combination of such substances with reagents may produce the change in reagent's color. One applicable way to utilize the invention is to use it to identify the biowarfare agents such as anthrax. Recently a demand in such devices increased dramatically after many instances across the country when the presence of suspicious powder-like substance was reported.

In most of such episodes law enforcement and/or health authorities were alarmed about the presence of unknown or suspicious powder-like substances. It was essential to establish whether the matter was in fact a dangerous biowarfare agent. As recent multiple reports of the uncovering of powder-like substance show, in each instance the unknown substance had to be subjected to an expensive and time consuming testing while the circumstances required an immediate answer whether the tested matter is in fact a biological agent. The authorities realized a great need in light, easy-to-carry, inexpensive, and simple in use device that could provide instantaneous testing results and to furnish public with sufficient certainty whether the substance generally is biohazard.

It is well known that many biowarfare agents include toxic and pathogen substances. One common ingredient found in many such toxic and pathogen substances, including anthrax, is at least one protein. Although the mere presence of a protein is not dispositive indication that the tested substance contains a hazardous biowarfare agent, the lack of protein may show that the tested sample is not likely to be toxic or pathogenic. On the other hand, if it is determined that the sample contains protein; such sample may be subjected to more specific tests to determine whether a particular pathogen or a toxin is present. Thus, one well-established method to learn whether the particular substance is biologically hazard is to conduct the protein-presence test.

The idea to use reagent's reaction to the presence of certain biowarfare agents, such as pathogens or toxins, is embodied in many inventions. One particular application of this method is an integral part of the Bradford protein assay. The Bradford assay is recommended for the general determination of protein content in a tested substance. Briefly, a Bradford assay based on the observation that the acidic solution of Coomassie Brilliant Blue G-250, generally known as Coomassie dye or Coomassie reagent, changes the color when exposed to a protein. The Bradford assay is one of many assays that the present invention may utilize.

According to general application of the Bradford assay, a tested sample is collected and then placed into a container. A Coomassie reagent is administered into the material in the container. The resulting contact of such reagent with tested substance may produce a change in color of the reagent as an indication of the presence in the substance of certain biological material, like, for instance, a protein, that is an indispensable part of the toxin or a pathogen. Once it is determined that such biological material is likely present in the substance, the sample may be subjected to further and more sophisticated tests to determine the specific nature of the substance.

SUMMARY OF THE INVENTION

The present invention is directed to an apparatus for detecting the presence of a protein. The detection may be performed in a reaction chamber where a material to be tested may be placed and where a mixture of a reagent and a tested material may actually occur. There is also a reservoir for reagent or for any other chemical substance that may be combined with a material to be tested, and optionally, a member that connects or secures a reaction chamber with said reagent reservoir. Such connecting or intermediate member may be a separate part of the invention or it may be a part of either reaction chamber or reagent reservoir.

It is essential that the result of the protein-detecting assay be as accurate as possible. Therefore, it is preferred that the user of the invention be assured immediately prior to conducting an assay that the reagent to be used is active. Because the device may utilize a Bradford regent that is capable of changing the color when exposed to the protein-containing substance, it would be reasonable to use the harmless protein-containing material, such as nylon, as a color-changing indicator before the reagent is applied to a tested material. Thus the invention may also have an end member or a tip with a piece of a nylon or other protein containing material attached to it. This nylon-wrapped tip may function as a source of a protein for testing the "freshness" of the reagent. The reagent should change color when it contacts the protein containing material indicator and may show that the reagent to be applied to the tested substance is in an active state when such nylon tip, once soaked by some of the reagent, changes color, for example, from white to blue, according to a Bradford assay.

The elements of the assembled device may be arranged in such way that the reagent, once forced from the reagent reservoir, may travel through and react with the nylon tip before the reagent contacts the material to be tested in the reaction chamber. This initial freshness test gives a user a positive indication that the result of the assay on the material in question will be accurate. The color change indicator member may be a separate part of the device or it may be a part of any other element of the device. The sizes and proportions of all elements of the invention may vary as desired.

Because it is preferred that the result of an interaction between elements in the reaction chamber may be observed after they are mixed, it is desired that the chamber is a clear tube with a base, although the reaction chamber may be a variety of different configurations.

It is preferable that a reagent reservoir, or at least one portion of it, be made from a flexible material to allow placing a desired amount of the reagent into a reaction chamber by, for example, squeezing it. It is also desirable that the reagent reservoir be transparent to allow observing a remaining supply of the reagent.

It is preferable that the distribution of the reagent from the reagent chamber occurs only when desired. Thus, to prevent an accidental discharge of a reagent from the reagent reservoir to the reaction chamber, the current invention may have a combination of the reagent reservoir with a narrow tubular portion extending from the reagent reservoir and a cone-shaped gasket in an end of the narrow tubular portion. Particularly, an end of the tubular portion of the gasket may insertably receive a cone-shaped gasket. The narrow tubular portion may provide efficient distribution of a reagent to the reaction chamber, and the cone-shaped gasket, while tightly inserted into the tubular portion of the reagent reservoir, may provide a desirable seal to prevent accidental discharge of surplus amounts of the reagent. In order to create a suitable seal between surfaces of the cone gasket and the interior wall surface of the tubular portion, the outer diameter of at least the base of the cone-shaped gasket may be at least about equal to an inner diameter of the tubular portion of the reagent reservoir.

Once a cone-gasket is frictionally inserted into the tubular portion, the resulting tightness between the outer surface of at least a portion of the gasket and the tubular portion creates a desirable watertight seal. At the same time, the cone-shaped gasket may have a small extension on its outer surface formed at least at one point where surfaces of the cone-shaped gasket and the tubular portion contact. One variation of such extension may be a mold seam developed on the outer surface of the cone-shape gasket extending preferably from the apex to the base. As a result of such extension or ridge, once the gasket is tightly inserted in the tubular portion, the surface of the cone gasket adjacent the ridge or extension may be slightly deflected inwardly from the inner surface of the tubular portion of the reagent reservoir at the point where the extension protrudes from the surface of the gasket and the resulting tightness of the contact between the outer surface of the cone-shaped gasket and the inner surface of the tubular portion of the reagent reservoir at this point would be less than at any other point of the contact between two surfaces, although the overall tension between named surfaces would remain sufficient enough to prevent relatively easy disjoint between cone-shaped gasket and tubular portion of the reagent reservoir. This configuration of the cone-shaped gasket and the tubular portion creates a seal between reagent reservoir and reaction chamber in order to prevent accidental leaks of the reagent, but when it necessary, an ample pressure, such as a finger pressure, applied to the reservoir, may force the reagent to percolate between the outer surface of the cone-shaped gasket and the inner surface of the tubular portion of the reagent reservoir, mostly at the point of the extension formed on the surface of the cone-shaped gasket where the tightness of the contacted surfaces of such gasket and the reagent reservoir is less, and thus to force the reagent to exit from the reagent reservoir in preferably small quantities such as one or more drops.

An alternative embodiment of the invention may also include a reagent applicator that may regulate the administering of the reagent into the reaction chamber. Such applicator may be installed between the reagent reservoir and the reaction chamber. Also, to provide better transportation and readily accessibility by individual users, the device may be equipped by a clip that may attach the device to clothing.

BRIEF DESCRIPTION OF THE DRAWINGS

FIG. 1 is a side view of the reagent reservoir.
FIG. 2 is a side view of the end member.
FIG. 3 is a side view of the cone gasket.
FIG. 4 shows a side view of the cap.
FIG. 5 is a side view of the reaction chamber.

DESCRIPTION OF THE PREFERRED EMBODIMENT

Figure 6:
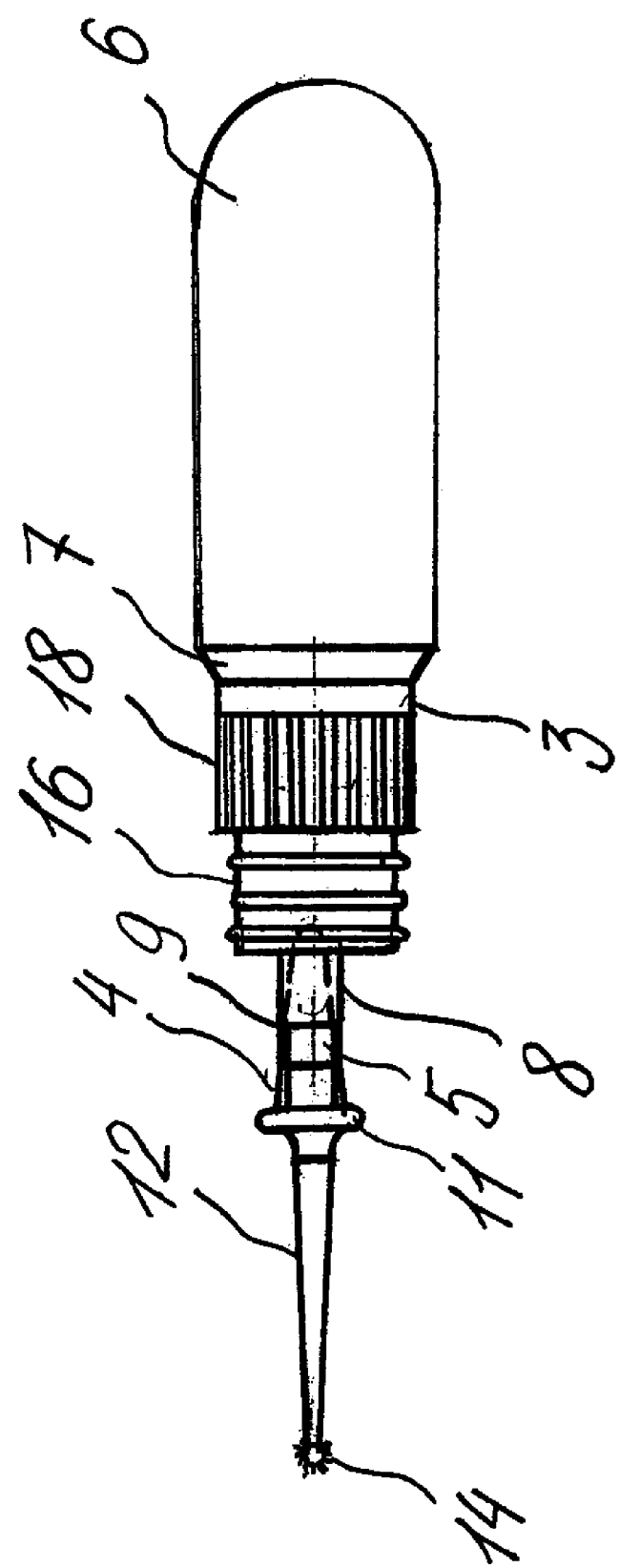
FIG. 6 is a side view of the reagent reservoir assembled with the cap, the cone gasket and the end member.
Figure 9:
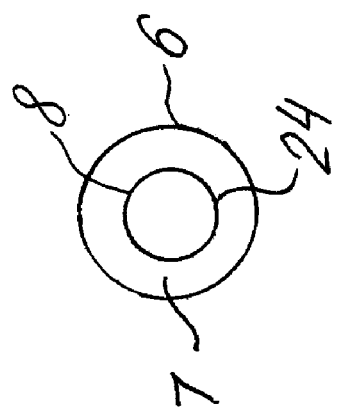
FIG. 9 is a rear view of the end member taken in the "b" direction.
Figure 7:
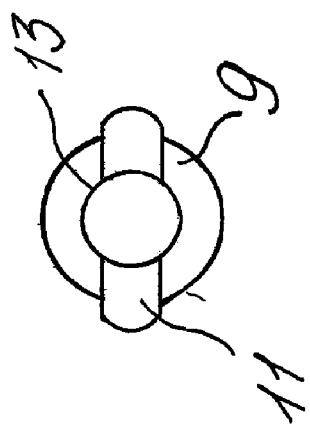
FIG. 7 is a front view of the end member taken in the "a" direction.
Figure 8:
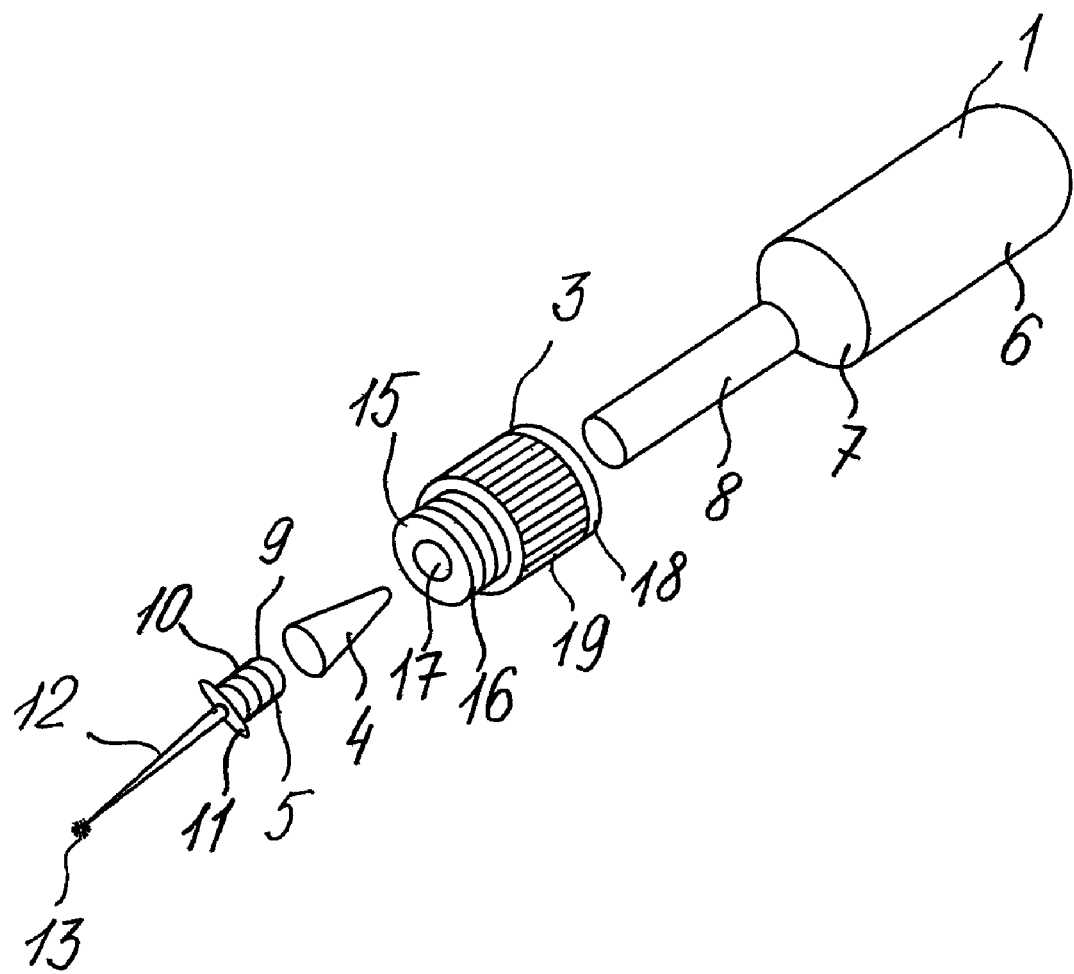
FIG. 8 shows the exploded prospective view of the device.

The preferred embodiment of the invention may have a reagent reservoir 1, a separate reaction chamber 2, a cap 3, a cone-shaped gasket 4, and an end member 5.

A reagent reservoir 1 may be a vessel for receiving a reagent that is used to test a substance. The reagent reservoir may be any suitable shape depending on the amount of a substance that is to be tested. As noted above, the reservoir is preferably made from a clear or transparent material so that the amount of reagent remaining can be ascertained. Alternatively, if desired only a portion of the reagent reservoir may be clear or transparent only so much of the reagent vessel would be clear give the user an idea of the amount of the reagent remaining. A suitable example of a reservoir is a pipette and the reservoir may have a squeezable portion 6, a neck portion 7 and a tubular portion 8. The tubular portion 8 may receive a cone-shaped gasket 4 which in turn may receive an end member 5.

In the preferred embodiment, the squeezable portion 6 of said reservoir 1 may be in a form of a plastic tube that is closed at one end and open at the other. It is preferable that the squeezable portion 6 be relatively soft and flexible that it would be possible to force reagent, drawn into the reservoir, out when pressure of fingers is applied to such squeezable portion 6. Also, it would be preferable if the squeezable portion 6 is transparent in order to observe the remaining amount of a reagent drawn into such squeezable portion 6.

Although the reagent reservoir 1 may have any shape, in order to achieve more efficient and gradual dispensing of the reagent, it is preferable that at least one portion of the reservoir be provided with a pipette-like narrow tubular portion 8. Thus, in one embodiment the invention may have a tubular portion 8 in a shape of a narrow tube at the end of the squeezable portion 6. It is preferred to have squeezable portion 6 larger in diameter than the tubular portion 8 mainly for generally two reasons. First, the relatively larger diameter of the squeezable portion 6 allows the reagent reservoir to have a capacity to accommodate larger amount of the reagent. This would provide an ability to carry amount of a reagent sufficient enough to supply reagent for several tests. It may be necessary where only single testing device is available and/or in remote areas where an immediate access to testing laboratories for additional supply of a reagent may not be available. In contrast, relatively smaller diameter of the narrow cylindrical tubular portion 8 of the reagent reservoir 1 would allow efficient distribution of the reagent to the reaction chamber 2. Each squeeze of the squeezable portion 6 preferably results in a relatively small amount of the reagent entering into the tubular portion 8 of the reagent reservoir 1. In conjunction with cone-shaped gasket 4, which is described below, the tubular portion 8 may produce a desirable small globule or drop of the reagent at the end of such tubular portion 8 of the reservoir 1. Therefore, the preferred embodiment of the reagent reservoir 1 may have two portions with contrasting diameters: the squeezable portion 6 and the tubular portion 8.

In order to prevent accidental and undesirable leaks from the reagent reservoir 1 to the reaction site, it is preferred that the open end of the tubular portion 8 be sealed and such seal may only be broken when a suitable pressure such as finger pressure is applied to the squeezable portion 6 of the of the reagent reservoir 1 and as a result of such pressure, the reagent is forced from the reagent reservoir 1 to enter the tubular portion 8 of the reagent reservoir 1 and pass through the interface between the cone shaped gasket and the inner surface of the tubular portion. Although various configurations of the sealant may be employed, in the preferred embodiment the open end of the tubular portion 8 may receive the cone-shaped gasket 4. Such cone-shaped gasket 4 is flexible and may be hollow inside. The cone-shaped gasket also may have a diameter at the base 21 at least equal to or slightly larger than the diameter 20 of the tubular portion 8 of the reagent reservoir 1 to provide a seal between outer surface of the cone-shaped gasket 4 and the inner surface of the tubular portion 8 once the cone-shape gasket is inserted, apex-forward, to the tubular portion 8 of the reagent reservoir 1. Thus, if the cone-shaped gasket 4 is inserted into the open end 20 of the narrow portion 8 of the reagent reservoir 1 and then pressed further to such point where the resistance to the thrust of the cone gasket 4 increases significantly, the resulting tension between the outer surface of the cone gasket 4 and the inner surface of the narrow portion 8 of the reagent reservoir 1 may provide desirable watertight sealant to prevent accidental discharge of the reagent into the reaction site or during transport of the device.

At the same time, the cone-shaped gasket 4 may have at least one relatively small extension or ridge 22 on its outer surface at least at a point where the surface of the gasket 4 contacts a portion of the inner surface of the tubular portion 8. The length of such extension 22 may be such that the extension is just a point or a line extending along a portion of the outer surface of the gasket. In a more preferred embodiment, the seam or ridge may extend from generally in the vicinity of the apex of the cone shaped gasket to generally in the vicinity of the base of the gasket. In a most preferred embodiment, the ridge extends from the apex to the base of the gasket. Although the ridge is shown as a straight line it is not required to be straight.

In one embodiment such extension 22 may be a mold seam, which may be a result of the molding process of the cone-shaped gasket 4 used during manufacture. When the cone gasket 4 is inserted into the open end 20 of the tubular portion 8 of the reagent reservoir 1 the apex of the cone-shaped gasket 4 faces toward the squeezable portion 6 of the of the reagent reservoir 1, and then pushed toward the squeezable portion until the resulting tension between the outer surface 23 of the cone gasket 4 and the inner surface 24 of the narrow portion 8 of the reagent reservoir 1 prevents further movement of the cone-shaped gasket 4. Even though the overall tension between the outer surface 23 of the cone-shaped gasket 4 and the inner surface 24 of the tubular portion 8 may form a watertight seal, the extension 22 may provide a less tight contact between the outer surface 23 of the cone gasket 4 and the inner surface 24 of the tubular portion 8 at the place where the extension 22 contacts the inner surface 24 of the narrow portion 8 of the reagent reservoir 1. Thus, although the tight contact between outer surface 23 of the cone-shaped gasket 4 and the inner surface 24 of the narrow portion 8 of the reservoir may prevent accidental leaks from the reagent reservoir 1 to the reaction site, the pressure, created inside the reagent reservoir 1 by squeezing the squeezable portion 6, forces the reagent to pass from the reservoir between surface 24 of the tubular portion 8 of the reservoir 1 and the outer surface 23 of the cone-shaped gasket 4 usually but not necessarily required at the point where the contact between surfaces is not tight due to the extension 22. The reagent thus is dispensed into the reaction site.

Friction between the named surfaces of the cone-shaped gasket 4 and the narrow portion 8 of the reagent reservoir 1 remains sufficient enough to prevent the cone-shape gasket 4 from being easily separated from the tubular portion 8 as a result of the pressure created in the tubular portion 8 by squeezing the squeezable portion 6. Thus, when the squeezable portion 6 of the reagent reservoir 1 is squeezed, the reagent is forced from the such squeezable portion 6 through the tubular portion 8 where it passes through the seal formed by tight contact between surfaces of the cone-shaped gasket 4 and the tubular portion 8 at the point where extension 22 protrudes from the outer surface of the cone-shape gasket 4. Such configuration of the elements of the device would allow a little small drop of the reagent to appear at the end 20 of the tubular portion 8 of the reagent reservoir 1 approximately at such part of the tubular portion 8 where extension 22 may contact with the inner surface 24 of the tubular portion 8.

The length of the cone gasket 4 may vary, but generally, the longer the cone-shape gasket 4 is, the wider is the area of a friction between the outer surface 23 of the cone-shaped gasket 4 and the inner surface 24 of the tubular portion 8 of the reagent reservoir 1, and as a result, the contact between the cone-shaped gasket 4 and the tubular portion 8 is tighter, thus the likelihood of the accidental leak from reagent reservoir 1 to the reaction site is lesser.

In order to conduct an assay to detect the presence of a protein in a tested material, it may be important to know whether the reagent is still active before such reagent is discharged into the reaction site. Although such pre-testing verification of the reagent may be performed in many ways and may be embodied in different configurations, because the reagent preferred to be used in this invention is an acidic solution of Coomassie Brilliant Blue G-250 which, when exposed to a protein-contained materials causes a visible color change, it would be reasonable to use some harmless type of protein-containing material to test the reagent.

It is generally known that a protein is found in a group of fibers known as polyamides. One type of polyamides that has widespread application is nylon. Because nylon contains protein, it may be practical to use nylon as a color changing indicator to test the viability of the reagent drawn into the reagent reservoir 1 before such reagent is exposed to tested material. Although such nylon indicator may be used in many embodiments, one used in this invention may be configured as a nylon micro-brush positioned on the tip of the end member 5.

It is preferred that the end portion 5 of the device is fixedly attached to the reagent reservoir 1 through a seal with the cone shaped gasket, in such way that when reagent is discharged from the squeezable portion 6 of the reagent reservoir 1 to the reaction site, the droplet of the reagent would travel down either through the end member 5 or along at least a portion of its outer surface and consequently, through or over the nylon micro-brush 14 attached to the tip 13 of said end member 5 and then to the reaction site. In such configuration, it would be possible for the reagent to moisten the nylon micro-brush 14 and thus to observe whether or not the micro-brush changes its color. If the reagent is active, the initially white nylon micro-brush turns blue as a result of the exposure to the Bradford reagent.

It is preferred that the nylon micro-brush is fixedly attached to the tip of the end member 5. End member 5 is open at each end and hollow throughout its length to permit reagent to flow through the end member or along a portion of its outer surface as described above from the reservoir to the micro-brush. Such configuration may simplify the reagent activity test and carrying the device around. In the preferred embodiment the end member 5 may have two portions. One portion 9 may insertedly received by the inner cavity of the cone-shaped gasket 4, and thus to attach the end member 5 to the reagent reservoir 1. Such portion may be configured as a cylinder or as a cone in shape although other shapes may be suitable for such portion. If the portion 9 is configured as a cylinder, then the diameter of said portion may be slightly smaller than the diameter of the base 21 of the cone gasket 4. Such configuration would allow the portion 9 of the end member 5 to be inserted into the inner cavity of the cone gasket 4 and once inserted and pushed inwardly until further movement of the end member 5 inside the cavity of the cone gasket 4 is resisted by the diminishing diameter of the cone-shape gasket 4. The resulting tension between inner surface of the cone gasket 4 and the outer surface of the cylindrical portion 9 of the end member 5 would allow the end member 5 to remain attached to the cone gasket 4, and thus, to the reagent reservoir 1. Additionally, the portion 9 of the end member 5 may have friction ribs 10 to provide tighter connection to the cone-shaped gasket 4. There may be on or more flanges 11 at the end of the cylindrical portion 9 of the end member 5 to limit the depth to which the portion 9 could be forced into the inner cavity of the cone gasket 4; such flanges may help to prevent excessive friction between the portion 9 and the cone-shaped gasket 4 and relatively easy disengagement of the cone-shaped gasket 4 and the end member 5. The possibility of such disengagement may be necessary in order to replace the end member 5 without replacing the entire device.

The second portion 12 of the end member 5 may be configured as an elongated tapered projection. In the preferred embodiment the projection 12 may be configured as an extended cone which has a base at the end of the portion 9 of the end member 5 with a small spherical tip 13 with a piece of nylon 14 wrapped around and glued to the tip 13 at the opposite side of the projection, although shape, length and width of the projection may vary. Such configuration of the projection is preferred because once the squeezable portion 6 of the reagent reservoir 1 is squeezed, the reagent from squeezable portion 6 would enter into the tubular portion 8 of the reagent reservoir 1 and then the reagent would leak between inner surface of the tubular portion 8 of the reagent reservoir 1 and the outer surface of cone-shape gasket 4 producing a small globule or drop of reagent at the end 20 of the tubular portion 8 of the reagent reservoir, the size and weight of such globule may be sufficient to induce the globule to travel down along the projection 12 of the end member 5, and further movement of the reagent result in an accumulation of said reagent in a form of a globular drop at the tip 13 of the end member 5. This would allow the small piece of nylon 14 wrapped around and glued to the tip 13 of the end member 5 to be moisturized with a reagent and to produce visible result that would allow to signal the state of activity of the reagent. Although a configuration and a method such piece of nylon 14 is attached to the tip 13 of the projection 12 may vary, the preferred embodiment include it as a fuzzy micro-brush glued around the spherical tip 13 of the end member 5.

The preferred embodiment of this invention may also have a reaction chamber 2 where tested substance may be collected and combined with the reagent. Because the observation of a result of assay may be necessary, it is preferred that the reaction chamber 2 is configured as a clear tube or other shaped receptacle.

It is preferred that the reagent reservoir 1 and the reaction chamber 2 may be assembled into a single unit. Although the way in which the reaction chamber 2 and the reagent reservoir 1 could be attached to each other may vary, the preferred embodiment may have a cap that may help to assemble together the reagent reservoir 1 and the reaction chamber 2. The cap 3 that may be fixedly positioned on the reagent reservoir 1 and may frictionally receive the reaction chamber 3. The cap 3 may be configured as an empty cylinder having two portions. One portion 15 may receive the reaction chamber 2. This portion may have friction ribs 16 to provide tighter connection between the outer surface of the cap 3 and the inner surface of the reaction chamber 2. The length of this portion 15 of the cap 3 may vary as long as it provides firm positioning of the reaction chamber 2 upon such portion 15.

In one embodiment, there may be an orifice 17 in the outer side of the cap through which the tubular portion 8 of the reagent reservoir 1 may be passed until the portion 18 of the cap 3 is pressed against the outer surface of the neck portion 7 of the reagent reservoir 1. To prevent further movement of the cap 3 along the reagent reservoir 1 once the cap 3 is positioned on the reagent reservoir 1, the diameter of the portion 18 of the cap 3 may be smaller that the wider diameter of the neck portion 7. Thus, such cap 3 may have shoulder formed on its surface as a difference between portions 15 and 18. The portion 18 of the cap 3 may also have multiple grooves 19 cut along the side surface and around the perimeter of this portion 18 of the cap for better grip should the reaction chamber 2 be detached from the reagent reservoir 1. Once the cap 3 is positioned on the reagent reservoir 1 to the point where the cap 3 is pressed against the neck portion 7 of the reagent reservoir 1, the cap 3 may be glued to the reagent reservoir 1 which may allow the cap 3 to be firmly attached to the reagent reservoir 1 and provide relatively easy attachment and detachment of the reaction chamber 2 to the reagent reservoir 1.

In operation, the reservoir containing a reagent may be squeezed by hand or subjected to mechanically applied pressure so that a quantity of reagent passes from the reagent reservoir between the outer surface of the cone shaped gasket and the tubular portion 8 the reagent can accumulate on the flanges 11 where it rests until there is a sufficient gravitational pull on the reagent to cause it to flow, usually in the form of a drop, down or along the second portion 12 of the end member 5 where it contacts the tip 13. Alternatively, the reagent can pass through an orifice in the end member 5 in the area, for example, of the flange 11 where the drop enters the interior of the end member 5 and passes through the end member 5 and exits from an orifice in the tip 13 where it can contact the nylon micro brush 14. In still another embodiment, the reagent can flow from the reservoir through the tubular portion 8 and into the end member where it passes from an orifice in the tip 13 to the brush 14.

Those skilled in the art will readily appreciate that many modifications of the exemplary embodiment are possible without materially departing from the novel teachings and advantages of this invention. For example, various configurations of the reagent reservoir 1, the reaction chamber 2, the gasket 4, the cap 3 or the end member 5 may be used. Alternative means may provide for the coupling of various parts of the invention. All such variations and modifications intended to be included within the scope if this invention as defined in the following claims.

Other modifications, substitutions, omissions and changes may be made in the design, size, materials used or proportions, operating conditions, arrangement or positioning of elements and members of the preferred embodiment without departing from the spirit of this invention as described in the following claims.

What is claimed is:

1. A protein detecting device comprising a reagent reservoir, said reagent reservoir having at least a portion thereof comprised of a material that is squeezable, said reagent reservoir having an end portion with a tubular member extending therefrom, said tubular member being hollow and in communication with said reservoir, said tubular member having an open end opposite said reservoir and said tubular member having a cone shaped gasket in said open end, said cone shaped gasket having a base and an apex, said apex of said cone shaped gasket being smaller than said base, said gasket having its base connected to an elongated member extending from said base of said gasket, said elongated member having a micro-brush at an opposite end of said elongated member.

2. The protein detecting device according to claim 1 wherein said cone-shaped gasket has at least one extension protruding from its outer surface.

3. The protein detecting device according to claim 1 wherein said elongated member has two portions a first portion of said elongated member has friction ribs for insertion into a portion of said base of said gasket.

4. The protein detecting device according to claim 1 wherein a second portion of said elongated member comprising the opposite end and having an elongated projection which ends in a tip.

5. The protein detecting device according to claim 4 wherein said tip member has a nylon micro-brush thereon.

6. The protein detecting device according to claim 5 wherein said first portion of said elongated member also has at least one flange wherein said flange may be used to limit the depth to which said first portion may be inserted into said base of said cone-shaped gasket.

7. A protein detecting device comprising a reagent reservoir, said reagent reservoir having at least a portion thereof comprised of a material that is squeezable, said reagent reservoir having an end portion with a tubular member extending therefrom, said tubular member being hollow and in communication with said reservoir, said tubular member having an open end opposite said reservoir and said tubular member having a cone shaped gasket in said open end, said cone shaped gasket having a base and an apex, said apex of said cone shaped gasket being smaller than said base, said gasket having its base connected to an elongated member extending from said open end of said gasket, said elongated member having a micro-brush at an opposite end of said elongated member; and said protein detecting device further comprising a cap wherein said cap may be fixedly positioned on said reagent reservoir.

8. The protein detecting device according to claim 7 wherein said cone-shaped gasket has at least one extension protruding from its outer surface.

9. The protein detecting device according to claim 7 wherein said elongated member has two portions a first portion of said elongated member has friction ribs for insertion into a portion of said base of said gasket.

10. The protein detecting device according to claim 7 wherein a second portion of said elongated member comprising the opposite end and having an elongated projection which ends in a tip.

11. The protein detecting device according to claim 10 wherein said tip member has a nylon micro-brush thereon.

12. The protein detecting device according to claim 11 wherein said first portion of said elongated member also has at least one flange wherein said flange may be used to limit the depth to which said first portion may be inserted into said base of said cone-shaped gasket.

13. The protein detecting device according to claim 12 wherein said cap is generally cylindrical in shape having two portions, a first portion of said cap which is adapted to receive a reaction chamber, and a second portion of said cap that is in contact with said tubular portion, said cap having an orifice that extends from said first portion of said cap to said second portion of said cap.

14. The protein detecting device according to claim 13 wherein said first portion of said cap may have at least one friction rib, said friction rib contacting an inner surface of said reaction chamber.

15. The protein detecting device according to claim 14 wherein said second portion of said cap has at least one groove located on an outer surface of said cap, wherein said groove provides gripping capability, wherein said groove extends from a rear end of said second portion of said cap to a front end of said first portion of said cap.

16. The protein detecting according to claim 15 wherein said rear end of said second portion of said cap comes into contact with a front outer surface of said reagent reservoir.

17. The protein detecting device according to claim 16 wherein said reagent is Coomassie Brilliant Blue G-250.

18. The protein detecting according to claim 7 or 17 wherein said reaction chamber is translucent.

19. The protein device according to claim 18 wherein said cap is glued to said reagent reservoir.

* * * * *